(12) United States Patent
Oberreit

(10) Patent No.: US 11,150,172 B2
(45) Date of Patent: Oct. 19, 2021

(54) ICE NUCLEII COUNTER TECHNOLOGY

(71) Applicant: Derek Oberreit, Roseville, MN (US)

(72) Inventor: Derek Oberreit, Roseville, MN (US)

(73) Assignee: Kanomax-FMT, Inc., White Bear Lake, MN (US)

( * ) Notice: Subject to any disclaimer, the term of this patent is extended or adjusted under 35 U.S.C. 154(b) by 0 days.

(21) Appl. No.: 16/252,901

(22) Filed: Jan. 21, 2019

(65) Prior Publication Data

US 2019/0154559 A1    May 23, 2019

Related U.S. Application Data

(62) Division of application No. 15/013,414, filed on Feb. 2, 2016, now abandoned.

(Continued)

(51) Int. Cl.
*G01N 15/02* (2006.01)
*G01N 15/06* (2006.01)
*G01N 33/18* (2006.01)
*G01N 15/14* (2006.01)
*G01N 1/42* (2006.01)

(52) U.S. Cl.
CPC ......... *G01N 15/0205* (2013.01); *G01N 15/02* (2013.01); *G01N 15/0227* (2013.01); *G01N 15/06* (2013.01); *G01N 15/0656* (2013.01); *G01N 15/1463* (2013.01); *G01N 33/18* (2013.01); *G01N 1/42* (2013.01);
(Continued)

(58) Field of Classification Search
CPC .......... G01N 15/0205; G01N 15/0227; G01N 15/06–0656; G01N 2015/0662–0693; G01N 21/53
See application file for complete search history.

(56) References Cited

U.S. PATENT DOCUMENTS 3,694,085 A * 9/1972 Rich .................... G01N 15/065
356/37
4,178,103 A * 12/1979 Wallace ............. G01N 15/0205
356/246

(Continued)

OTHER PUBLICATIONS

Lab on a Chip, Miniaturization for chemistry, physics, biology & bioengineering. vol. 9, No. 16, Aug. 21, 2009, "A microfluidic apparatus for the study of ice nucleation in supercooled water drops". Claudiu A. Stan, Gregory F. Schneider, Sergey S. Shevkoplyas, Michinao Hashimoto, Mihai Ibanescu, Benjamin J. Wiley.*

(Continued)

*Primary Examiner* — Alexander A Mercado
(74) *Attorney, Agent, or Firm* — Skinner and Associates; Joel D. Skinner, Jr.

(57) ABSTRACT

A method and system of measuring the size distribution of particles within dilute colloids, for example, through variation of the minimum ice-nucleation sizes of particles within the colloid. The system for measuring particles in fluids includes, a sample fluid inlet and an ice nuclei counter communicatively connected to the sample fluid inlet, the ice nuclei counter cooling the sample fluid and measuring particles which form crystals in the cooled fluid. The method for measuring particles in fluid includes the steps of providing a sample fluid, cooling the sample fluid, and measuring particles which form crystals in the cooled fluid.

7 Claims, 3 Drawing Sheets

Related U.S. Application Data

(60) Provisional application No. 62/110,683, filed on Feb. 2, 2015.

(52) U.S. Cl.
CPC ............... *G01N 2015/0681* (2013.01); *G01N 2015/0693* (2013.01); *G01N 2015/1486* (2013.01)

(56) References Cited

U.S. PATENT DOCUMENTS

| | | | | |
|---|---|---|---|---|
| 2003/0082825 A1* | 5/2003 | Lee | G01N 15/0255 | 436/148 |
| 2004/0225249 A1* | 11/2004 | Leonard | A61M 1/14 | 604/4.01 |
| 2005/0172476 A1* | 8/2005 | Stone | B01F 3/0807 | 29/592.1 |
| 2005/0272159 A1* | 12/2005 | Ismagilov | B01F 5/0646 | 436/34 |
| 2006/0076295 A1* | 4/2006 | Leonard | A61M 1/14 | 210/645 |
| 2008/0283775 A1* | 11/2008 | Doak | A01N 1/02 | 250/492.1 |
| 2011/0056273 A1* | 3/2011 | Gorbunov | G01N 15/065 | 73/28.01 |
| 2011/0114190 A1* | 5/2011 | Wen | B01L 3/502784 | 137/1 |
| 2011/0284770 A1* | 11/2011 | Nakada | G01N 15/147 | 250/459.1 |
| 2011/0313725 A1* | 12/2011 | Hayashi | G01N 15/1429 | 702/176 |
| 2012/0286171 A1* | 11/2012 | Hoshishima | G01N 21/6408 | 250/459.1 |
| 2013/0186269 A1* | 7/2013 | Cheng | B01D 53/228 | 95/47 |
| 2014/0170697 A1* | 6/2014 | Sharpe | G01N 15/1436 | 435/30 |
| 2014/0200164 A1* | 7/2014 | Makarewicz, Jr. | B01F 13/0062 | 506/12 |
| 2014/0342397 A1* | 11/2014 | Andersen Gad | G01N 1/40 | 435/34 |
| 2015/0125944 A1* | 5/2015 | Olson | G01N 15/1404 | 435/288.7 |
| 2015/0132766 A1* | 5/2015 | Yasuda | G01N 21/6458 | 435/7.1 |
| 2015/0268140 A1* | 9/2015 | Wang | G01N 15/0227 | 356/335 |
| 2016/0041080 A1* | 2/2016 | Spencer | G01N 15/1031 | 73/61.71 |
| 2016/0084814 A1* | 3/2016 | Olson | G01N 33/1886 | 435/288.7 |

OTHER PUBLICATIONS

Journal of the Atmospheric Sciences vol. 52. No. 11 (1924), "A New Look at Homogeneous Ice Nucleation in Supercooled Water Drops". H.R. Pruppacher.*

* cited by examiner

ICE NUCLEII COUNTER TECHNOLOGY

CROSS-REFERENCE TO RELATED APPLICATIONS, IF ANY

This application is a divisional of application Ser. No. 15/013,414, filed Feb. 2, 2015, which claims the benefit under 35 U.S.C. § 119(e) U.S. Provisional Patent Application Ser. No. 62/110,683, filed Feb. 2, 2015, which is hereby incorporated by reference.

37 C.F.R. § 1.71(e) AUTHORIZATION

A portion of the disclosure of this patent document contains material which is subject to copyright protection. The copyright owner has no objection to the facsimile reproduction by anyone of the patent document or the patent disclosure, as it appears in the U.S. Patent and Trademark Office patent file or records, but otherwise reserves all copyright rights whatsoever.

STATEMENT REGARDING FEDERALLY SPONSORED RESEARCH OR DEVELOPMENT

Not applicable.

REFERENCE TO A MICROFICHE APPENDIX, IF ANY

Not applicable.

BACKGROUND

1. Field

The present invention relates, generally, to systems, apparatus and methods for analyzing material. More particularly, the invention relates to methods and apparatus for measuring the size distribution and number concentrations of particles in colloids. Most particularly, the invention relates to methods and apparatus for measuring the size distribution and number concentrations of particles within dilute colloids through variation of the minimum detected size of colloid particles. The technology is useful, for example, for colloid characterization, filter testing, and high purity water system monitoring.

2. Background Information

Existing technology in this field is believed to have significant limitations and shortcomings. Systems used to measure particle size distributions in colloids are limited to particle diameters greater than 20 nm, when such colloids are present at very low concentrations in ultrapure liquids. Small particles are a major problem for the semiconductor device manufacturing industry. Particles smaller than 50 nm can significantly reduce manufacturing yield of present day semiconductor devices. The ability to measure the size distribution and number concentrations, especially low concentrations, of these particles is highly desired.

A brief summary of the state of the art of particle detection is provided in U.S. Pat. No. 8,272,253 to Grant et al. entitled Particle Concentration Measurement Technology and U.S. Pat. No. 8,573,034 to Grant et al. entitled Residue Concentration Measurement Technology. Pruppacher, A New Look at Homogeneous Ice Nucleation in Supercooled Water Drops, *Journal Of the Atmospheric Sciences*, Vol. 52, No. 11 (1924) discloses information on ice nucleation. Stan et al. A microfluidic apparatus for the study of ice nucleation in super cooled water drop, *Lab On A Chip*, Vol. 9, No. 16 (2009). also discloses information on ice nucleation.

All U.S. patents and patent applications, and all other published documents mentioned anywhere in this application are incorporated by reference in their entirety.

BRIEF SUMMARY

The present invention provides analysis methods and apparatus which are practical, reliable, accurate and efficient, and which are believed to constitute an improvement over the background technology. In the preferred embodiment, the invention relates to an apparatus and method where colloid particles are detected using an Ice Nuclei Counter (INC) with a temporally or spatially varying detection threshold diameter. In the preferred embodiment, the sample introduced to the INC may consist of the unaltered source colloid, a colloid downstream of a sample introduction device, or downstream of a colloid concentrator (employing evaporation and/or cross flow filtration).

In one aspect, the invention relates to an INC where the minimum nucleated particle size is varied by adjusting the degree of supercooling which is temporally varied by adjusting the temperatures of the chilled flow cell. These temperatures may either be adjusted in a stepwise manner or continuously ramped.

In another aspect, the invention relates to a INC where the degree of supercooling is spatially varied where the colloid is exposed to an increasing degree of supercooling. Larger particles (where the onset of ice nucleation growth occurs at a lower degree of supercooling) will form crystals earlier in the flow cell path. By detecting the position of the ice crystal within the flow cell, size information may be inferred.

The present invention is believed to involve novel elements, combined in novel ways to yield more than predictable results. The problems solved by the invention were not fully recognized in the prior art.

The aspects, features, advantages, benefits and objects of the invention will become clear to those skilled in the art by reference to the following description, claims and drawings.

BRIEF DESCRIPTION OF THE SEVERAL VIEWS OF THE DRAWING

The present invention, and the manner and process of making and using it, will be better understood by those skilled in the art by reference to the following drawings.

DETAILED DESCRIPTION

The present invention provides a system and method for determining the number concentration and size distribution of particles within a dilute colloid. This is achieved by detecting the formation of ice crystals in a supercooled suspension liquid. In this description, "ice" is used as a general reference to the solid phase of any liquid and is not limited to water. For high purity liquids which are free of large particles, the temperature at which a liquid changes to the solid phase may occur at a lower value than otherwise observed for a standard 'bulk' liquid (referred to as supercooling). This is because the thermodynamic barrier for a liquid-solid phase transition at the bulk freezing point is not energetically favorable without the presence of nucleation sites. Particles within a liquid may serve as suitable nucleation sites and the formation of ice within a supercooled liquid provides evidence of a particle within that liquid. The temperature $T_n$, at which a particle with radius a will provide a suitable nucleation site is given by (Pruppacher, A New Look at Homogeneous Ice Nucleation in Supercooled Water Drops, Journal Of the Atmospheric Sciences, Vol. 52, No. 11 (1924).):

$$\frac{T_{wi}}{T_n} = \frac{2M_w \sigma_{ls}}{L_m \rho_i a} \quad \text{(Eq. 1)}$$

where $T_{wi}$ is the bulk freezing temperature, $M_w$ is the molecular weight, $\sigma_{ls}$ is surface tension, $L_m$ is the latent heat of melting, and $\rho_i$ is the density of ice.

The concentration of nucleated particles is then measured by detecting the ice crystals using established light scattering methods. As is evident in Equation 1, the temperature at which a particle will serve as an ice nucleation 'seed' decreases with decreasing particle size. Therefore, at a given supercooled liquid temperature, the number of detected ice crystals represents the cumulative concentration of particles within the liquid larger than the corresponding minimum nucleated particle size.

Figure 1:
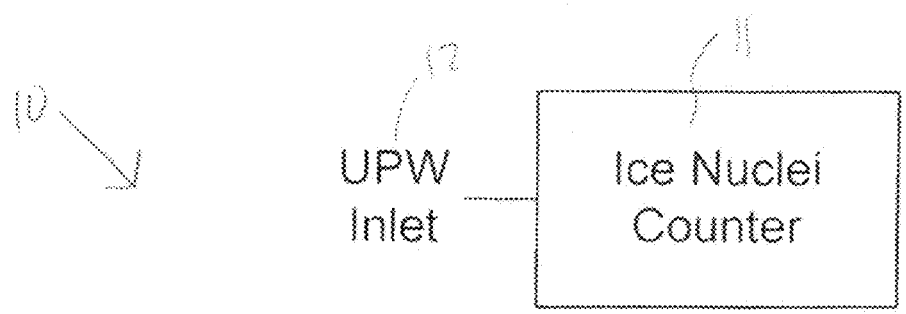
FIG. 1 is a schematic representation of an embodiment of the particle size distribution and number concentration system of the present invention, with no upstream colloid modification.
Figure 2:
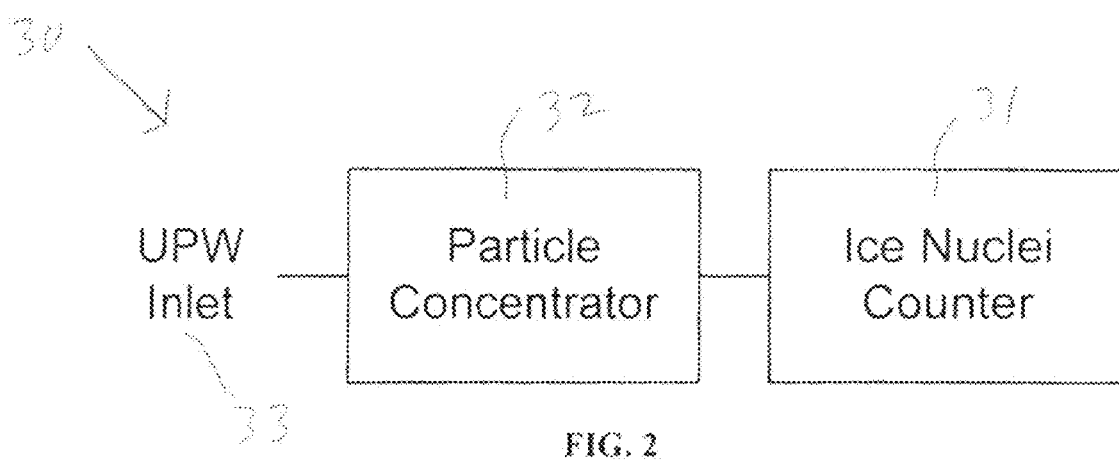
FIG. 2 is a schematic representation of an embodiment of the system additionally employing a particle concentrator.
Figure 3:
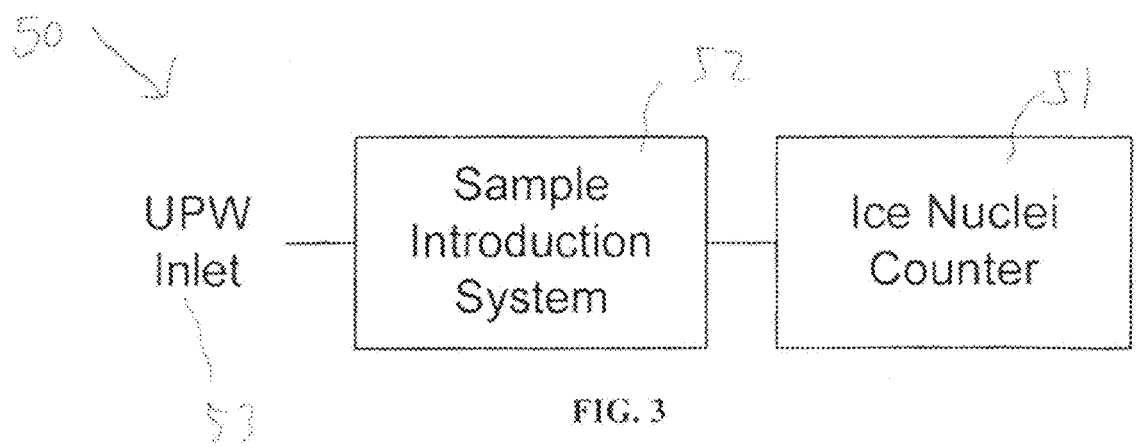
FIG. 3 is a schematic representation of an embodiment of the system employing a colloid introduction device.

FIGS. 1-3 show embodiments of configurations of the system of the invention for measuring size distribution and number concentration of particles in colloids, including unaltered colloids, diluted colloids and concentrated colloids.

In FIG. 1, an ultra pure water (UPW) sample is unaltered. The system 10 includes an ice nuclei counter 11 connected to a fluid inlet 2, for example an ultra pure water inlet. This configuration 10 is most useful for monitoring ultrapure water systems for particles. This configuration is also beneficial for testing size dependent particle breakthrough for water filters (where a colloid is introduced upstream of the filter).

Referring to FIG. 2, the sample is modified by concentrating the particles within the colloid. The system 30 includes an ice nuclei counter 31 connected to a particle concentrator 32, which is connected to a fluid inlet 33 (ultra pure water or ultrapure water). Ultra pure water is a dilute colloid and typically contains less than 1 ppb of non-volatile residue where the concentration of particles greater than 10 nm in diameter is less than 1e6#/ml. This configuration 30 results in reduced statistical error for low concentrations by increasing the effective sampled volume. Methods and devices for concentration include, but are not limited to, solvent evaporation and cross flow filtration. One method of evaporation includes evaporating the fluid sample through a semi porous membrane such as a porous PTFE membrane (for example a Zeus Corp membrane). Other means of evaporation include bathing the sample in hot dry gas or exposing the liquid sample surface to a hot dry gas.

In the embodiment of FIG. 3, the sample is modified by injecting a higher concentration colloid into a clean solvent stream. The system 50 includes an ice nuclei counter 51 connected to a sample introduction system 52 which is connected to a fluid inlet (ultra pure water). This technique is useful for characterizing the particle size distribution of the high concentration colloid. A colloid of known concentration is used to calibrate the inspected volume of the INC device.

Figure 4:
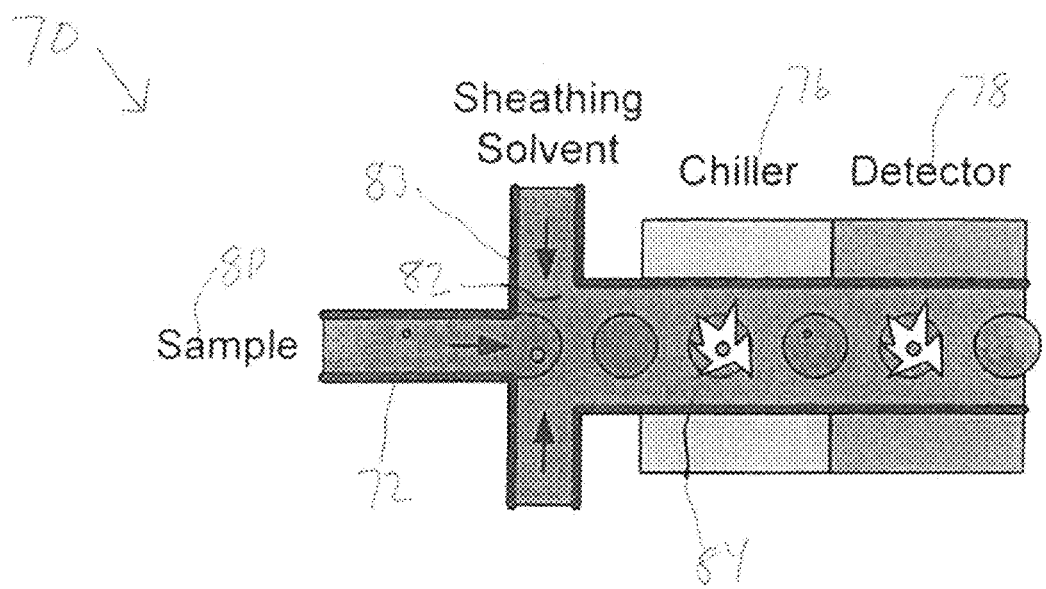
FIG. 4 is a schematic representation of an embodiment of an ice nucleation cell, used with the system.
Figure 5:
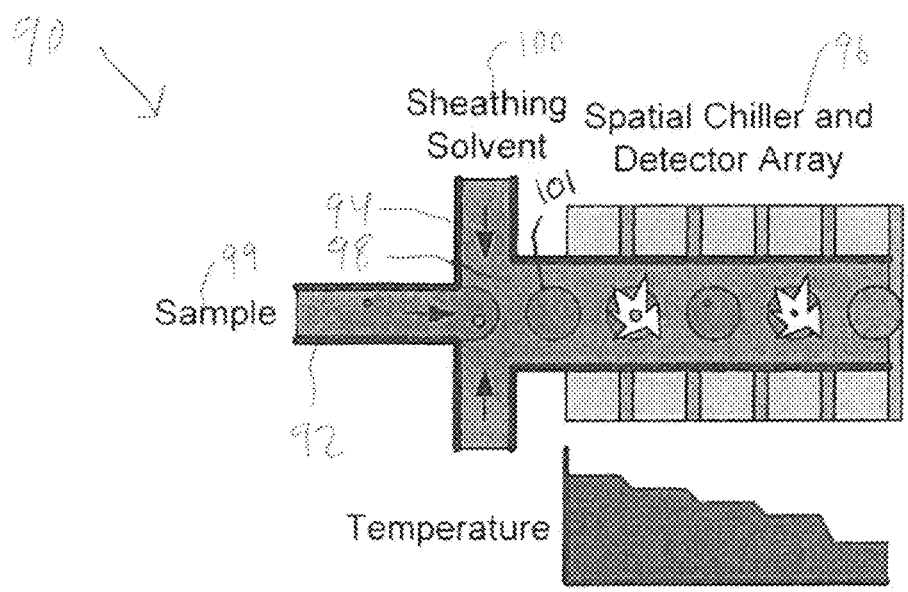
FIG. 5 is a schematic representation of an embodiment of an ice nucleation cell, with spatially varying nucleation zones.

FIGS. 4-5 show embodiments of an ice nuclei counter cell used in the systems 10, 30 and 50 above. In both Figures, the water stream is sheathed in a secondary liquid whose properties include low miscibility with the primary sample stream and a freezing temperature lower than the minimum critical nucleation temperature probed by the system. Preferably, this sheathing liquid is a fluorinated solvent such as FLOURINERT coolant liquid or a NOVEC engineered fluid. The heterogeneous liquid stream is then cooled to a controlled temperature and the resulting ice crystals are detecting using established optical light scattering methods.

In the embodiment of FIG. 4, the liquid stream 80 is cooled to a set temperature. The ice nuclei counter 70 comprises a sample fluid inlet 72 connected to a sheathing fluid inlet 74, a chiller 76 and a detector 78. The chiller and detector 78 define a nucleation cell 84 having a wall there around. The detection is preferably an optical ice crystal detector. Optical detection may be based on light scattering or direct imaging. It is within the purview of the invention that electrical (for example capacitive) and acoustic (for example ultrasound) ice crystal detection and counting devices may be used. This set temperature may be temporally varied to adjust the minimum detected colloidal particle size. Temporal variation may be incremental with non-sampled periods allowing for steady state conditions, or continuous with active control and or monitoring of the temperature within the nucleation region to calculate the minimum detected particle size.

FIG. 5 shows an embodiment of the ice nucleation cell where the degree of supercooling is spatially varied with progressively colder sections. By detecting the number of ice nuclei present at each section, a cumulative size distribution is inferred. The ice nuclei counter 90 includes a sample fluid inlet 92 connected to a sheathing fluid inlet 94 and to a spatial chiller and detector array 96.

Figure 6:
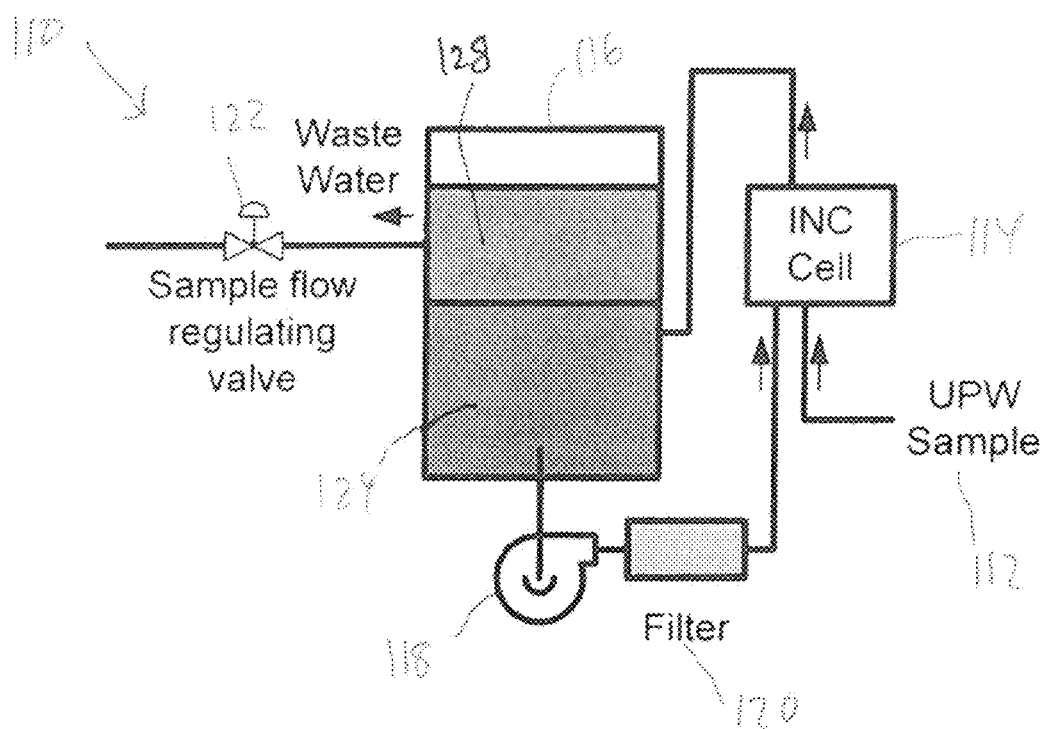
FIG. 6 is a schematic representation of an embodiment of the system with colloid sample introduction to the flow cell as well as a fluorinated solvent recycler.

FIG. 6 shows an embodiment of a system 110 including an assembly for recycling the sheathing liquid. The system 110 includes a sample fluid inlet 112 connected to an ice nuclei counter 114. A holding tank 116 is connected to the outlet of the cell 114. A pump 118 is connected to the bottom outlet of the tank 116 and then to the cell 114 via a filter 120. Waste water exits the tank 116 via a sample flow regulating valve 122. Use of a sheathing liquid with low miscibility with the primary sample liquid will result in separation of the two liquids with the lower density liquid located above the higher one of higher density. This illustrates a condition where the sheathing liquid has the higher density. The liquid is introduced to the flow cell by the pump 118 with the filter 120 located downstream to remove any particles. The rate of sheathing solvent delivery may be regulated by modulating the pump 118 speed or by use of a valve (not shown) downstream of the pump 118. The primary sample waste stream is allowed to pass out of the system though the valve 122 which regulates the total primary sample flow through the cell 114.

Referring again to FIGS. 1-5, the systems 10, 30 and 50 include an ice nucleation cell 70 or 90 and a liquid delivery means 12, 32 and/or 52, and an optional sheathing fluid recovery system 116 (see FIG. 6). The ice nucleation cells 70 or 90 consist of a region 82/98 which sheathes the sample stream 80/99 with an immiscible liquid 83/100 which has a freezing temperature lower than the minimum temperature set in the flow cell. This two part sample stream 84/101 is then directed to a region which cools the stream to a set temperature (below the freezing temperature (bulk freezing temperature) of the sampled liquid) where particles larger than a specific size will serve as ice nucleation sites. The 'nucleated' particles are then easily detected by established light scattering devices 78/96 and methods. The degree of supercooling may be temporally or spatially varied to change the minimum nucleated particle size and provide size distribution information. Supercooling variations both temporal and spatial, can be discrete or continuous. Referring to FIG. 6, the sheathing liquid recovery system collects the sample as it exits the nucleation cell 114 and allows for separation of the sample and sheathing liquids. The sheathing liquid 124 is then filtered and reintroduced to the nucleation cell 114. The sample waste 128 is allowed to drain from the system 110.

The invention provides a method and system for determining the quantitative size distribution of particles in a colloid by measuring the number and concentration of particles which form ice crystals in a supercooled liquid. In the preferred embodiments, the apparatus includes an ice nucleation cell where the sample stream is sheathed in an immiscible liquid with a sufficiently low freezing point.

In one variation, the two part sample stream is cooled to a set temperature which is lower than the bulk freezing temperature of the inner sample stream (supercooling) where:

a. the sample stream is temperature is controlled by varying the temperature of the nucleation cell walls:
  i. wherein the temperature is held at a fixed point and ice crystals are detected, or
  wherein the temperature is adjusted in a stepwise, manner and the ice crystal detection or measurement is made after reaching steady temperature states, or
  iii. wherein the temperature is adjusted and measured throughout the transition period and the minimum nucleated particle size or detection limit is inferred from the measured temperatures utilizing Equation 1, or
b. the detection limit is varied by adjusting the temperature of the sheathing liquid stream:
  i. wherein the temperature is adjusted in a stepwise manner and the ice crystal measurement is made at each step after reaching steady temperature state, or
  ii. wherein the temperature is adjusted and measured throughout the transition period where the detection limit is inferred from the measured temperatures.

In another variation, the two part sample stream is spatially cooled to progressively lower temperatures below the bulk freezing temperature of the inner sample stream (supercooling) where the sample stream is temperature is controlled by varying the temperature of the nucleation cell walls in discrete sections, and
  i. wherein the temperatures are held at a fixed point and then ice crystals are detected, or
  ii. wherein the temperatures are adjusted in a stepwise manner and the ice crystal measurement is made after reaching steady temperature states, or
  ii. wherein the temperatures are adjusted and measured throughout the transition period and the detection limits are inferred from the measured temperatures.

The embodiments above are chosen, described and illustrated so that persons skilled in the art will be able to understand the invention and the manner and process of making and using it. The descriptions and the accompanying drawings should be interpreted in the illustrative and not the exhaustive or limited sense. The invention is not intended to be limited to the exact forms disclosed. While the application attempts to disclose all of the embodiments of the invention that are reasonably foreseeable, there may be unforeseeable insubstantial modifications that remain as equivalents. It should be understood by persons skilled in the art that there may be other embodiments than those disclosed which fall within the scope of the invention as defined by the claims. Where a claim, if any, is expressed as a means or step for performing a specified function it is intended that such claim be construed to cover the corresponding structure, material, or acts described in the specification and equivalents thereof, including both structural equivalents and equivalent structures, material-based equivalents

What is claimed is:

1. An apparatus for measuring a size distribution and a concentration of very small particles less than 20 nm in diameter in ultrapure water, a dilute colloid for semiconductor device manufacturing, comprising,
   an ultrapure water inlet for input of a ultrapure water;
   a particle concentrator connected to the ultrapure water inlet, the particle concentrator being selected from the group consisting of an evaporative concentrator, and a cross flow filter;
   an ice nuclei counter communicatively connected to the particle concentrator downstream of the particle concentrator, the ice nuclei counter cooling the ultrapure water and measuring particles less than 20 nm in diameter which form crystals in the cooled ultrapure water generated by the ice nuclei counter, the ice nuclei counter comprising:
     a sheathing fluid inlet communicatively connected to the ultrapure water inlet for sheathing the ultrapure water in an immiscible sheathing fluid and generating a sheathed ultrapure water stream, the immiscible sheathing fluid having a predetermined freezing temperature,
     a nucleation cell, having one wall surrounding the nucleation cell, for passage of the sheathed ultrapure water stream, the nucleation cell having an upstream first section and a downstream second section,
     a chiller for temporally, adjustably cooling the nucleation cell, and thereby generating a cooled sheathed ultrapure water stream, the chiller being disposed around the nucleation cell wall at the first section, and
     a detector for detecting crystals in the cooled sheathed ultrapure water stream in the ice nuclei counter, the detector being disposed at the second section of the nucleation cell downstream of the chiller; and
   wherein, in use, the sheathed ultrapure water stream is first cooled to a predetermined set first temperature which is lower than a freezing temperature of the ultrapure water stream, whereby it is supercooled, and ice crystals are formed, and wherein a temperature of the ultrapure water stream is then temporally varied to adjust a minimum detected colloidal particle size; and
   wherein the ice nuclei counter measures size distribution and concentration of particles in the ultrapure water, and wherein the ice nuclei counter measures particles less than 20 nm in diameter.

2. The apparatus of claim 1, wherein the sheathing fluid is selected from the group of fluids consisting of FLOURINERT coolant liquid and NOVEC engineered fluid.

3. The apparatus of claim 1 wherein the detector is an optical detector.

4. The apparatus of claim 1, wherein the temperature of the sheathed sample fluid is varied, by varying the temperature of the nucleation cell via the chiller, and measured throughout a transition period and the minimum detected colloidal particle size is inferred from the measured temperatures.

5. The apparatus of claim 1, further comprising a sheathing fluid recovery assembly connected to an outlet of the ice nuclei counter and to the sheathing fluid inlet, whereby sheathing fluid is captured at the outlet of the ice nuclei counter, processed, and returned to the ice nuclei counter.

6. The apparatus of claim 5, wherein the sheathing fluid recovery assembly includes a tank, connected to the outlet of the ice nuclei counter, wherein sample fluid and sheathing fluid separate, sheathing fluid is drawn from the bottom of the tank by a pump, cleaned by a filter, and recycled to the ice nuclei counter, and waste sample fluid drains from the assembly.

7. An apparatus for measuring a size distribution and concentration of very small particles less than 20 nm in diameter in ultrapure water, a dilute colloid for semiconductor device manufacturing, comprising,
 a. a inlet for input of a sample fluid;
 b. a particle concentrator connected to the inlet, the particle concentrator being selected from the group consisting of an evaporative concentrator, and a cross flow filter;
 c. an ice nuclei counter communicatively connected to the particle concentrator, the ice nuclei counter cooling the ultrapure water and measuring particles which form crystals in the cooled ultrapure water, the ice nuclei counter comprising:
  i. a sheathing fluid inlet communicatively connected to the ultrapure water inlet for sheathing the ultrapure water in an immiscible sheathing fluid and generating a sheathed ultrapure water stream, the immiscible sheathing fluid having a predetermined freezing temperature,
  ii. a nucleation cell, having one wall surrounding the nucleation cell, for passage of the sheathed ultrapure water stream the nucleation cell having an upstream first section and a downstream second section,
  iii. a chiller for temporally, adjustably cooling the nucleation cell, and thereby generating a cooled sheathed ultrapure water stream, the chiller being disposed around the nucleation cell wall at the first section, and
  iv. a detector for detecting crystals in the cooled sheathed ultrapure water stream, the detector being disposed at the second section of the nucleation cell downstream of the chiller; and
 wherein the sheathed ultrapure water stream is cooled to a predetermined temperature which is lower than a freezing temperature of the ultrapure water stream, whereby it is supercooled, the ice crystals are formed, and wherein the temperature of the ultrapure water stream is then temporally varied to adjust a minimum detected colloidal particle size;
 wherein the ice nuclei counter measures the size distribution of particles and the concentration of particles in the ultrapure water, and wherein the ice nuclei counter measures particles less than 20 nm in diameter; and
 d. a sheathing fluid recovery assembly including a tank connected to an outlet of the ice nuclei counter, wherein sample fluid and sheathing fluid separate, sheathing fluid is drawn from the tank and recycled to the ice nuclei counter, and waste sample fluid drains from the assembly.

* * * * *